United States Patent [19]

Wong

[11] 4,412,997
[45] * Nov. 1, 1983

[54] INSECT REPELLENT COMPOUNDS

[75] Inventor: Rayman Y. Wong, Richmond, Calif.

[73] Assignee: Stauffer Chemical Company, Westport, Conn.

[*] Notice: The portion of the term of this patent subsequent to Sep. 7, 1999, has been disclaimed.

[21] Appl. No.: 329,365

[22] Filed: Dec. 10, 1981

[51] Int. Cl.³ .................... A01N 43/40; C07D 213/55
[52] U.S. Cl. ........................... 424/263; 424/DIG. 10; 546/342
[58] Field of Search ...................... 424/263, DIG. 10; 546/342

[56] References Cited

U.S. PATENT DOCUMENTS 3,192,193 6/1965 Altscher et al. .................... 424/170
3,409,626 11/1968 Cavallito et al. ................... 424/246

OTHER PUBLICATIONS

Boyer et al., VACS, vol. 80, pp. 2741–2743 (1958).
Hankovszky et al., Journal of Medicinal Chemistry, vol. 9, No. 1, pp. 151–153 (1966).
Mikhlina et al., Chemical Abstracts, vol. 52, No. 12863i (1958).
Idemitsu Kosan, Chemical Abstracts, vol. 94:59792d.

Primary Examiner—Jerome D. Goldberg
Assistant Examiner—Freda Abramson
Attorney, Agent, or Firm—Joel G. Ackerman

[57] ABSTRACT

Compounds having the formula

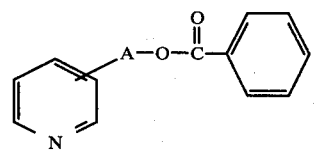

in which A is $C_1$–$C_3$ alkylene, are effective insect repellents.

8 Claims, No Drawings

INSECT REPELLENT COMPOUNDS

This invention relates to repelling insects by the use of compounds having the formula

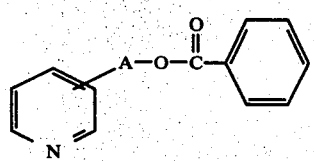

in which A is a straight or branched-chain alkylene group having from 1 to 3 carbon atoms. The compounds are particularly useful for repelling flying insects, especially mosquitoes, from lighting and/or feeding.

In general the compounds may be prepared by reaction of an appropriate pyridyl alkanol with a benzoyl halide (preferably benzoyl chloride):

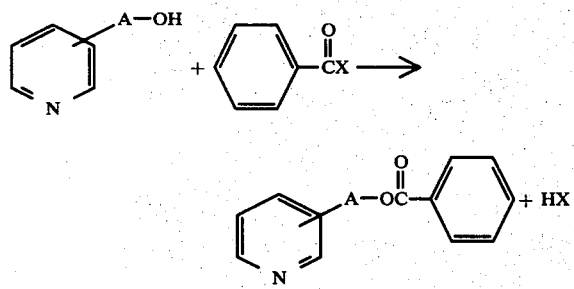

in which X is halogen.

This reaction is generally conducted at temperatures of about 0° to about 15° C., in the presence of a solvent such as methylene chloride, and a base, preferably an amine such as triethylamine or pyridine.

The following represents an example of the preparation of a compound of this type.

EXAMPLE

In a flask there were mixed, with stirring, 5.0 g. (0.036 mole) 3-(3-pyridyl)-1-propanol, 2.9 g. pyridine and 50 ml. methylene chloride. The resulting solution was cooled to 0° C., then 5.1 g. (0.036 mole) benzoyl chloride was added at such a rate as to maintain the temperature at about 15° C. When the reaction was complete, the mixture was warmed to room temperature and stirred for 1 hour.

The resulting solution was washed with water, saturated aqueous sodium bicarbonate, water, saturated aqueous sodium chloride and dried over sodium sulfate. The organic layer was filtered through dry sodium sulfate and the solvent removed under vacuum. There was obtained 7.2 g. (82% of theoretical yield) of pyridyl 3-propyl benzoate, $n_D^{30}$ 1.5510 (Compound 3 herein).

The following Table I contains a list of representative compounds of this invention.

Structures of these compounds were confirmed by spectroscopic analyses.

TABLE I

| Compound No. | Position On Pyridine Ring | A | $n_D^{30}$ |
|---|---|---|---|
| 1 | 3- | —CH$_2$— | 1.5667 |
| 2 | 2- | —(CH$_2$)$_2$— | 1.5548 |
| 3 | 3- | —(CH$_2$)$_3$— | 1.5510 |
| 4 | 2- | —(CH$_2$)$_3$— | 1.5500 |

Insect Repellent Tests

The compounds in Table I were tested for insect repellency by the following procedures:

Mosquito:

A paper cup filled with pupae of the mosquito *Culex pipiens quinquefasciatus* (Say) was placed in a screened cage and the pupae allowed to emerge into adults. Sugar cubes were then saturated with 1.0 milliliter (ml) of an acetone solution containing 0.1 wt. % of the test compound, and, for a control, with the same amount of acetone alone. After the cubes dried they were put into the screened cage. Repellency was determined by the number of mosquito adults lighting and feeding on the sugar cubes, with observations being made daily for 5 days after treatment. The number of days of complete repellency of mosquitos from the sugar cubes was recorded.

Comparative tests were similarly conducted using the compound N,N-dimethyl-m-toluamide, commercially manufactured and employed as an insect repellent, generally known by the generic name "deet". The results of the tests of deet and the compounds of Table I are shown in the following Table II. The numbers in each column represent the number of days of complete repellency observed using the specified concentration.

TABLE II

| Compound No | Days Repelled, 0.1 wt. % |
|---|---|
| 1 | 6 |
| 3 | 3 |
| deet | 1 |
| control | 0 |

Housefly:

The insect utilized for this test was the housefly, *Musca domestica* (L.). One hundred houseflies of mixed sexes were placed in test cages. In each cage was placed a sugar cube saturated with 1.0 ml of acetone containing 1 wt. % of the test compound. The cube was dried and weighed before being placed in the cage. Each cage also contained a water-saturated cotton plug to provide moisture. The test cages were placed on a turntable and rotated at 1.5 revolutions per minute to keep the flies randomly distributed inside the cage. After 48 hours the flies in each cage were anesthetized with carbon dioxide. The sugar cubes were removed and reweighed and the percentage weight loss (due to consumption by the flies) recorded. A repellency ratio, calculated as the percent weight loss of the treated sugar cube divided by the percent weight loss of a control sugar cube containing only acetone and no test compound, was calculated. The lower the repellency ratio, the greater the repellency of the test compound. The repellency ratios of the test compounds are shown in the following Table III. Values given for the repellency ratio represent an average of from one to three replications per compound.

TABLE III

| Compound | Repellency Ratio: Concentration 1 wt. % |
|---|---|
| 1 | 0.74 |
| 3 | 1.04 |
| deet | 0.60 |

Stable Fly; Yellow Fever Mosquito

Insects utilized for these tests were the stable fly, *Stomoxys calcitrans* and yellow fever mosquito, *Aedes aegypti*.

Pupae of these insects were placed in separate standard fly cages and allowed to emerge into adults. The mosquitoes were supplied with a sugar-water solution; the stable flies with water, sugar cubes, and casein. Tests on mosquitoes were performed at least 3 days after the adults emerged; those on stable flies, one day after emergence because of the short life span (4–5 days) of these flies without a blood meal.

Test compounds were weighed and dissolved in acetone. One milliliter (ml) of the test solution was pipetted onto a 9×9 cm. swatch of cotton stocking. The swatches were then allowed to dry for 1 hour.

A square opening 6×6 cm. was made in an upper corner of one side of each fly cage. A large, hard cardboard disk was placed over the opening so that it could be rotated to either cover or expose the opening as desired. One-half of the disc was left intact. In the remaining half, several 6×6 cm. square openings were cut. When the intact half of this disc was located over the opening in the fly cage, this opening was effectively sealed.

Swatches of treated stocking were placed over the square holes in the disc and held in place by metal frames attached to magnetic tape.

To initiate the test, the disc was rotated so that a treated swatch became located over the opening in the cage. The palm of the tester's hand was placed over a cardboard ring, 8 cm. in diameter and 1 cm. thick. The ring acted as a spacer and protected the hand from bites which could otherwise be inflicted by the insects. A breath of air was exhaled through tubing into the opening, so that insects could be attracted to the swatch by the warm, moist air and the tester's hand. The number of insects landing on the swatch was observed, and the number probing, recorded during a 1-minute exposure. Repellency was considered to occur when 5 or fewer insects probed in swatch during the exposure.

The compounds were tested at applications rates ranging from 0.1 mg/cm$^2$ of swatch downwards. The results of these tests on stable flies (SF) and yellow fever mosquitoes (YFM) are contained in Table IV.

TABLE IV

| Compound | Repellent Concentration, mg/cm$^2$ | |
|---|---|---|
| | SF | YFM |
| 2 | >0.1 | 0.1 |
| 3 | >0.1 | >0.1 |
| 4 | >0.1 | 0.1 |

The novel compounds of this invention may be used as insect repellents in either diluted or undiluted form. When used in a diluted form, the compounds may be embodied in compositions containing relatively high or relatively low concentrations of the active compound. For example, the active compound can be incorporated into two relatively high concentration compositions such as wet sprays or solutions in alcohol or other suitable solvents. Such compositions may contain, in addition to the active compound, adjuvants such as emulsifying agents, surface active agents, anti-oxidants and propellants which may be found normally in insect repellent preparations. The active compounds of this invention may be employed as the sole active components of such compositions or may be used in admixture with other compounds having a similar or different utility. For example, the compounds may be incorporated into creams, lotions, powders, suntan oils, insecticides and other preparations which may contain pesiticidal or other useful substances, as well as into compositions of various types used for treating fabrics or articles of clothing to render them insect repellent. In general, compositions for repellent use may contain from 0.5 up to 80 weight %, preferably from 2 to about 40 weight %, of the novel active compounds.

Examples of typical formulations employing compounds of this invention are for instance, Example 1: Emulsifiable Concentrate

| Component | Weight % |
|---|---|
| Compound 1 | 53.6 |
| Aromatic Hydrocarbon Solvent | 36.4 |
| Emulsifier | 10.0 |
| Total | 100.0 |

Example 2: Lotion

| Component | Weight % |
|---|---|
| Compound 2 | 10.7 |
| Lanolin | 4.8 |
| Mineral oil | 8.0 |
| Trihydroxyethylamine stearate | 1.8 |
| Glycosterin | 0.8 |
| Glycerine | 4.6 |
| Sodium benzoate | 1.0 |
| Water | 68.3 |
| Total | 100.0 |

Example 3: Alcohol Solution

| Component | Weight % |
|---|---|
| Compound 3 | 53.6 |
| Isopropanol | 46.4 |
| Total | 100.0 |

Example 4: Alcohol Solution

| Component | Weight % |
|---|---|
| Compound 4 | 80.0 |
| Ethanol | 20.0 |
| Total | 100.0 |

Example 5: Wettable Powder

| Component | Weight % |
|---|---|
| Compound 3 | 26.9 |
| Hydrated calcium silicate | 62.1 |
| Sodium lignosulfonate | 5.0 |

| Component | Weight % |
| --- | --- |
| Orzan A (mixture of ammonium lignosulfonate and wood sugars) | 5.0 |
| Wetting agent | 1.0 |
| Total | 100.0 |

What is claimed is:

1. A method of repelling insects from a locus to be protected therefrom, comprising applying to said locus an effective insect repelling amount of a compound having the formula

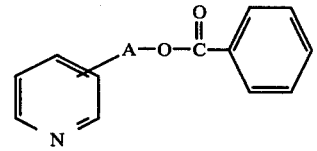

in which A is an alkylene group having from 1 to 3 carbon atoms.

2. A method according to claim 1 in which the compound is applied in an amount effective to repel mosquitoes.

3. A method according to claim 2 in which the mosquito is yellow fever mosquito.

4. A method according to claim 1 in which A is methylene.

5. A method according to claim 1 in which A is ethylene.

6. A method according to claim 1 in which A is trimethylene.

7. A method according to claim 1 in which the side chain is substituted on the pyridine ring at the 3-position.

8. A method according to claim 1 in which the side chain is substituted on the pyridine ring at the 2-position.

* * * * *